(12) United States Patent
Goodall et al.

(10) Patent No.: US 8,706,514 B1
(45) Date of Patent: Apr. 22, 2014

(54) CASE MANAGEMENT SYSTEM AND METHOD FOR MEDIATING ANOMALY NOTIFICATIONS IN HEALTH DATA TO HEALTH ALERTS

(75) Inventors: Colin Goodall, Rumson, NJ (US); Guy Jacobson, Bridgewater, NJ (US); Simon Tse, Holmdel, NJ (US); John Mark F. Mocenigo, Califon, NJ (US); Richard Drechsler, Morristown, NJ (US)

(73) Assignee: AT&T Intellectual Property II, L.P., Atlanta, GA (US)

( * ) Notice: Subject to any disclaimer, the term of this patent is extended or adjusted under 35 U.S.C. 154(b) by 1908 days.

(21) Appl. No.: 11/253,164

(22) Filed: Oct. 18, 2005

(51) Int. Cl.
*G06Q 50/00* (2012.01)

(52) U.S. Cl.
USPC ............... 705/2; 600/300; 703/2; 703/11

(58) Field of Classification Search
USPC .................. 600/300; 703/11, 2; 705/2
See application file for complete search history.

(56) References Cited

U.S. PATENT DOCUMENTS

| | | | | |
|---|---|---|---|---|
| 5,769,074 A | * | 6/1998 | Barnhill et al. | 600/300 |
| 6,238,337 B1 | * | 5/2001 | Kambhatla et al. | 600/300 |
| 7,249,006 B2 | * | 7/2007 | Lombardo et al. | 703/2 |
| 7,266,484 B2 | * | 9/2007 | Lombardo et al. | 703/11 |
| 2003/0101076 A1 | * | 5/2003 | Zaleski | 705/2 |

OTHER PUBLICATIONS

Nobre F F, Detecting abnormal patterns in public health surveillance data with a probability index function, Biomedical Engineering Program, Federal University of Rio de Janeiro, published in 1992, IMIA.*
Nobre F F, A monitoring system to detect changes in public health surveillance data, International Journal of Epidermiology, 1994.*
Google patents search, Nov. 21, 2013.*

* cited by examiner

*Primary Examiner* — Dilek B Cobanoglu
(74) *Attorney, Agent, or Firm* — Scott P. Zimmerman, PLLC

(57) ABSTRACT

A system and method for mediating anomaly notifications in health data to health alerts using data structures and logic to organize, contain, and disposition identified health anomalies. Multiple generators of anomaly notifications operating asynchronously and independently can be processed. The case manager organizes anomaly notifications and supports collaborative decision making among users with diverse areas of expertise.

20 Claims, 7 Drawing Sheets

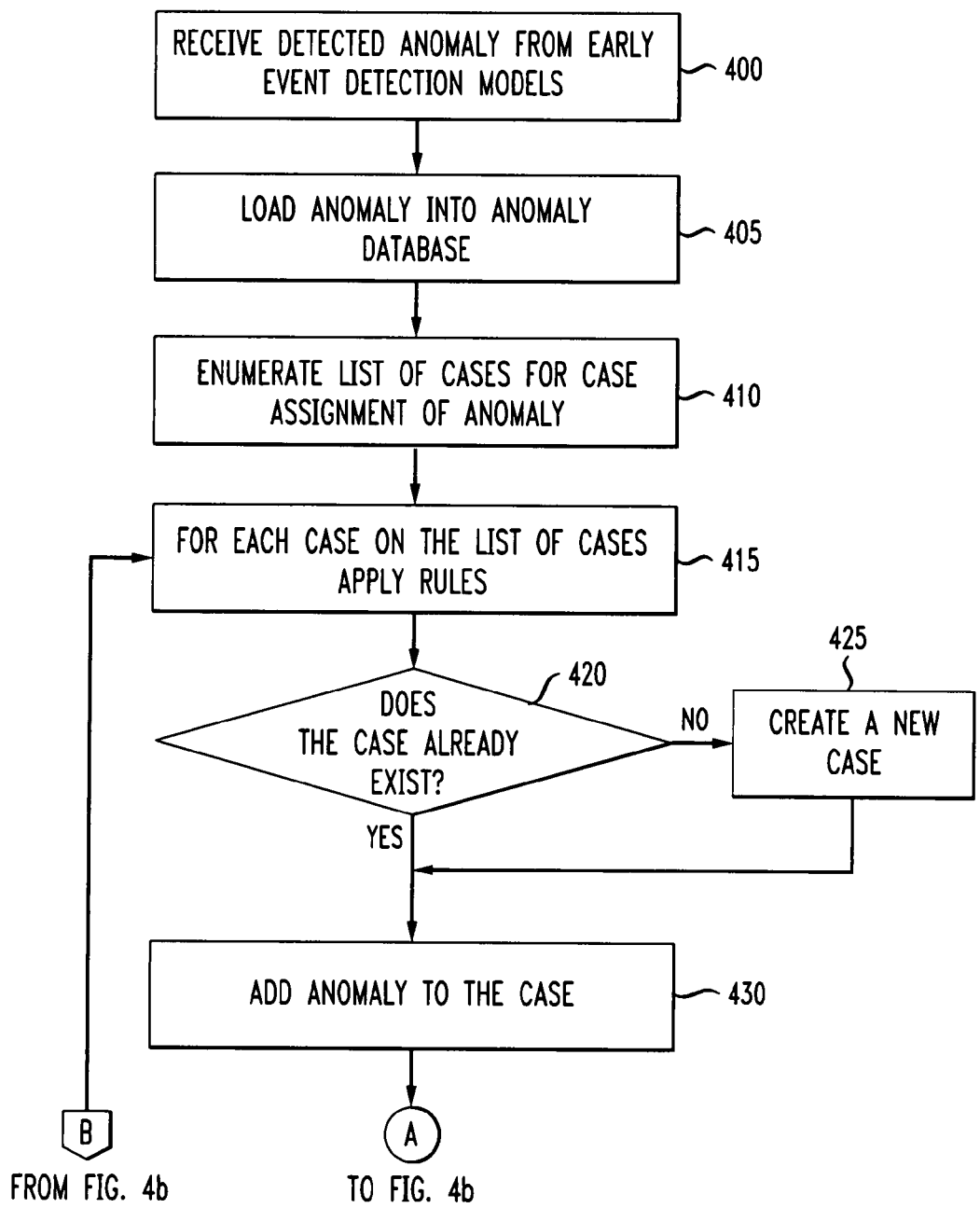

CASE MANAGEMENT SYSTEM AND METHOD FOR MEDIATING ANOMALY NOTIFICATIONS IN HEALTH DATA TO HEALTH ALERTS

BACKGROUND

The invention relates generally to the field of biosurveillance. More specifically, embodiments of the invention relate to systems and methods for mediating anomalies found in health data to health alerts.

Biosurveillance is the monitoring of the biological and health status of a population for changes against norms established by historical data for that population including changes against trends or established cyclic patterns in the data. An anomaly or aberration occurs when the status is markedly different from the associated norm. When this occurs, a system for biosurveillance may generate an anomaly notification, or what is commonly referred to as an anomaly. Presently, the ability of public health care systems to monitor health data and trends in the data so as to identify anomalies and to manage the anomaly notifications tends to be antiquated and slow.

An anomaly in health data can be characterized by anomaly variables. Anomaly variables include location—for example, one or more towns, ZIP codes, cities, counties, states, etc.; medical context—for example, influenza, West Nile virus, gastro-intestinal complaints, etc.; time frame—one or more days; additional covariates—for example, age and gender; measures of severity; the algorithm by which the anomaly was discerned, and security content.

In surveillance of health data, numerous conditions lead to an anomaly notification, ranging from a single patient with a specific condition, to a pattern in the data detected by a statistical method. An anomaly notification is not per se actionable, but if one or more anomaly notifications are followed by a health alert, then that alert can be a trigger for various health and public safety measures. In determining how to respond to anomaly notifications and whether to issue an alert, various experts are involved. The experts may include data experts, statistical experts, epidemiologists, public health officials, and others.

Both public and private health care organizations face the challenge of developing an effective system for anomaly detection and management of anomaly notifications. For example, the Centers for Disease Control (CDC) have stated their intention to incorporate multiple anomaly detection algorithms into their surveillance system known as BioSense.

BioSense provides an integrated national view for electronic biosurveillance. The BioSense application augments local or regional surveillance systems with additional data, jurisdictional views, and analytic techniques to further characterize an outbreak or event. The data may also be combined with other data sources to provide a more complete picture of the health status of that geography or metropolitan area. While the CDC makes use of a health alert network, they do not presently have a case manager system.

New computer information systems are actively being developed to monitor data from various sources and of various types, from emergency room admissions information to over-the-counter (OTC) sales of pharmaceuticals. These systems look for patterns that might not be apparent to individual doctors or pharmacists, but might indicate an event of health concern such as the beginnings of a disease outbreak.

The need for consolidated regional and national public safety data has been expressed repeatedly by government agencies including the CDC, the Department of Defense, Homeland Security, and the Department of Health and Human Services, among others. The National Association of State EMS (Emergency Medical Systems) Directors has called for biosurveillance systems to be implemented throughout the healthcare and public safety systems.

Data management and combining data from multiple sources are important components in a biosurveillance system. For example, complete EMS data is missing at the regional and state level. Detection of acute or covert terrorist attacks requires an effective linking of data from a variety of sources, and an effective public health response will depend on the timeliness and quality of communication.

SUMMARY OF THE INVENTION

Although there are various anomaly identification methods and systems that assist health care professionals and government agencies, such systems are not completely satisfactory. The inventors have discovered that it would be desirable to have more automated systems and methods for mediating anomaly notifications in health data to health alerts.

The invention comprises systems and methods for mediating anomaly notifications in health data to health alerts using data structures and logic to organize, contain, and dispose of identified health anomalies. Multiple detection algorithms, operating asynchronously and independently, run against one or more health data streams. Examples of data streams are electronic laboratory requisitions and results, OTC sales of medicines and medical supplies, emergency department visit data, and others. The outputs of anomaly detection generators—anomaly notifications (anomalies)—are processed by the invention. The case manager organizes anomaly notifications and supports collaborative decision making and disposition among expert users.

The invention implements a case, which contains and organizes related anomalies where the anomalies share one or more of location (spatial), time frame (temporal), medical context, and additional covariates with each other anomaly mapped to that case. The case inherits variables such as location, medical context, time frame, additional covariates, measures of severity, algorithm, and security content from the anomalies it contains. Each received anomaly belongs to at least one case. A case includes associated case events which are time-stamped and include adding an anomaly to the case, user interactions, and user-driven or automated case disposition. The case supports collaboration, including notations, permissions, and an individual investigator taking "ownership" or primary responsibility for that case. The case further defines the scope of the detail data associated with the case and its included anomalies.

One aspect of the invention provides methods for mediating anomaly notifications in health care data to cases, and then to health alerts. Methods according to this aspect of the invention preferably start with receiving at least one anomaly, the anomaly including anomaly variable data, classifying the received anomaly, organizing the received anomaly into at least one case, where the case is a container for anomaly variable data and other data, providing an interactive environment for collaboration, dispositioning the case based upon results of the collaboration, and retiring the case.

Another aspect of the method is creating entries in a table of events associated with the case, extracting detail health data records associated with the case, and issuing an alert in response to the disposition.

Another aspect of the method of the invention is defining and managing dynamic work lists, each work list comprising a set of cases specific to individual users selected according to anomaly variables such as case location, medical context, time frame, priority, and data streams. The work list provides an interface to case and data detail for one or more individual cases on the work list. The scope, size, and sort order of the work list is determined by the user.

Yet another aspect of the invention is defining cases using ad hoc queries. Two variants are to define an ad hoc case as a container for specific data detail and to define an ad hoc case as a container for a set of anomalies.

A further aspect of the invention is an interface to a system for data visualization.

Other objects and advantages of the methods and systems will become apparent to those skilled in the art after reading the detailed description of the preferred embodiments.

BRIEF DESCRIPTION OF THE DRAWINGS

FIGS. 4a, 4b and 4c is a block diagram of an exemplary method according to one embodiment of the invention.

DETAILED DESCRIPTION OF THE PREFERRED EMBODIMENTS

Figure 1:
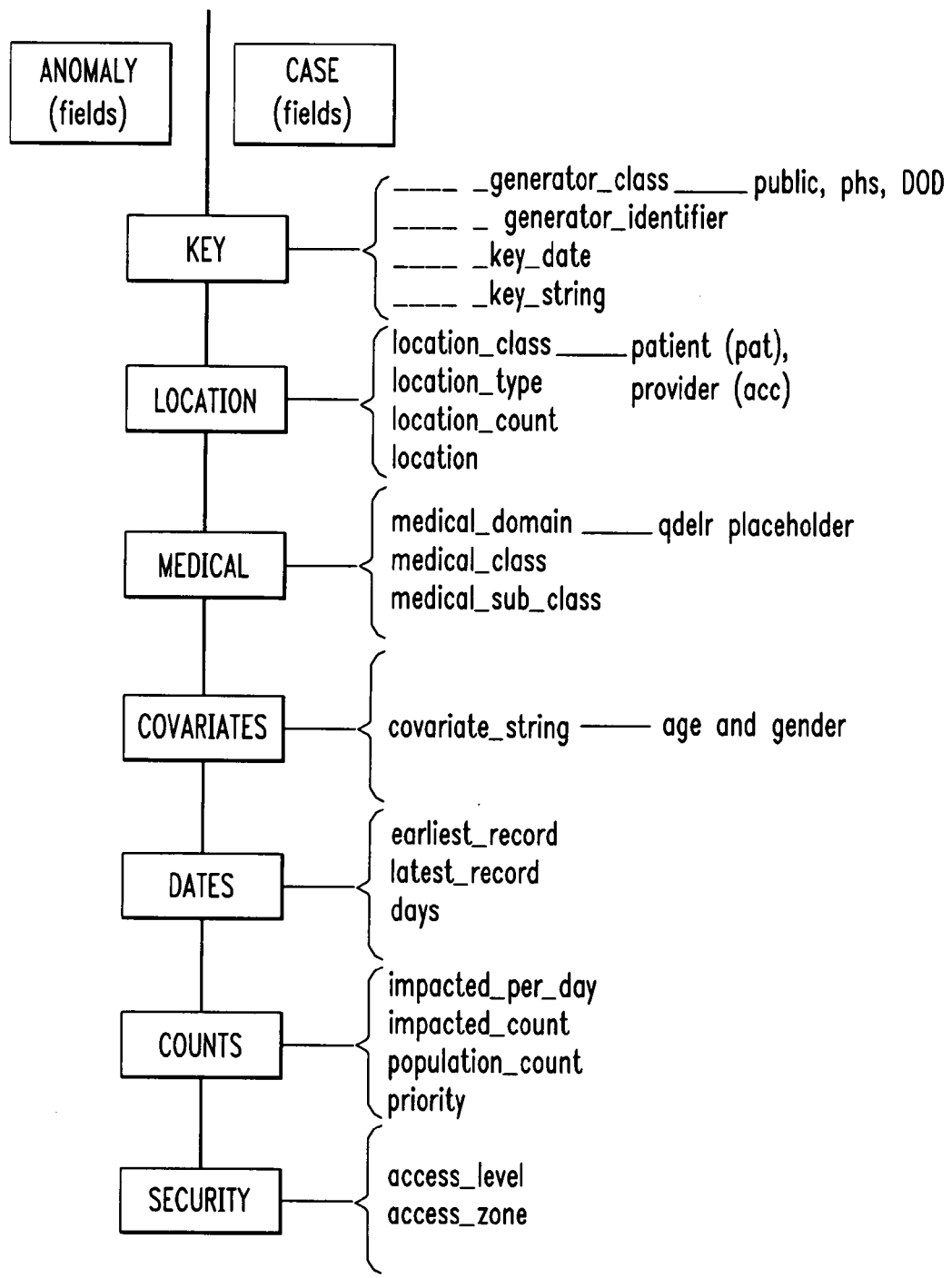
FIG. 1 is a diagram of an exemplary anomaly and case data structure.

Embodiments of the invention will be described with reference to the accompanying drawing figures wherein like numbers represent like elements throughout. Further, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. The terms "mounted," "connected," and "coupled" are used broadly and encompass both direct and indirect mounting, connecting, and coupling. Further, "connected" and "coupled" are not restricted to physical or mechanical connections or couplings.

It should be noted that the invention is not limited to any particular software language described or implied in the figures. One of skill in the art will understand that a variety of alternative software languages may be used for implementation of the invention. It should also be understood that some components and items are illustrated and described as if they were hardware elements, as is common practice within the art. However, one of ordinary skill in the art, and based on a reading of this detailed description, would understand that, in at least one embodiment, components in the method and system may be implemented in software or hardware.

Embodiments of the invention provide methods, systems, and a computer-usable medium storing computer-readable instructions for a case manager that organizes anomaly notifications and supports collaborative decision making between anomalies found in health data. In determining how to respond to anomaly notifications and whether to issue an alert, the invention application functionality allows a variety of experts in the fields of medicine, statistics, epidemiology, public health, and others to store, access and collaborate on a plurality of individual records regarding health data trends ranging from a single patient with a specific condition, to a pattern in the data detected by a statistical method and render a disposition.

The invention is a modular framework and is deployed as software as an application program tangibly embodied on a program storage device. The application is accessed through a graphical user interface (GUI). The application code for execution can reside on a plurality of different types of computer readable media known to those skilled in the art. Users access the framework by accessing the GUI via a computer.

The case manager system and method comprises data structures and logic executed in computer code for automatically combining anomaly notifications into cases for expert disposition. Cases are containers for one or more anomaly notification. Master cases can include other cases. Case manager events include case creation, anomaly notification classification, user interaction/collaboration, case disposition and case retirement.

The invention provides two major functions. The first is the organization of each received anomaly out of a potentially large number of received anomalies into one or more cases. Cases inherit the anomaly variables location, medical context, time frame, additional covariates, severity, and security context. Cases can be related to one another through shared or overlapping geography, medical context, and time frame.

The second function is to provide a work environment in which expert users with diverse backgrounds in epidemiology, statistics, public health, and the original data sources, can interact with each other in the dispositioning of each case.

The case manager of the invention comprises (I) Anomaly, Case, AnomalyCase, Event, Annotation and Alert data structures, (II) associated logic, part of which is embodied in the AnomalyCaseMap data structure, and (III) supporting metadata including data dictionaries and links to data dictionaries, and geographical mapping files and links to geographical mapping files.

Event data provides an activity log including received anomalies, case creation and expert user interaction. Every action and operation is recorded as an event in the Event data structure. Events include activities such as anomaly notifications received by the case manager, anomaly assignment/case creation, opening a case for review or disposition, annotations, a different user disposing of a case, the case manager retiring a case that has aged out, and others actions.

The Annotation data structure includes notes added by users including hyperlinks to other data and metadata.

The Anomaly and Case data structures are shown in FIG. 1. Data fields common to anomalies and cases comprise key, location, medical (context), covariates, dates (range), summary statistics (including counts) and security, in conjunction with key fields which identify cases and anomalies.

The AnomalyCase data structure specifies the membership of each anomaly in one or more cases, and conversely, the set of anomalies contained in each case.

The Alert data structure collects information related to the case for which one or more alerts are generated. The alert data structure is designed to interface to a health alert network.

Case manager logic sets forth the rules for assigning an anomaly to one or more cases, for combining common anomaly data fields, and for generating common fields for cases. Aside from the above common data fields, Anomaly and Case data tables have additional fields that are unique to each table. Typically, a case can be in one of several (non-exclusive) states, including available, open, closed, retired, and alerted. The case manager logic includes rules for transition between states, prompted either by user actions or by system events, for example, aging rules.

Common Data Fields

Anomaly notification, case generation and alerting are implemented in several modules of the case manager system. Anomaly notifications, cases, and alerts have in common several sets of fields:

- key—provides unique identifiers for anomalies and cases, and supports horizontal partitioning of the data tables for security and efficiency.
- location—describes the primary geographical extent of the anomaly, case, and alert.
- medical—describes the medical context.
- covariates—adds additional covariates such as age and gender.
- dates—describes the date range of the impacted data and includes the time of day.
- counts—number of impacted subjects and statistics for priority and relevance.
- security—fields related to security, defaulting to ePHI (electronic Protected Health Information) as defined by HIPAA (Health Insurance Portability & Accountability Act).

Common Key Fields anomaly/case_generator_class (STR)
anomaly/case_generator_identifier (STR)
anomaly/case_key_date (DATE)
anomaly/case_key_string (STR)
anomaly/case_description (STR)

generator_class and key_date are used for horizontally partitioning the data tables. The generator_class data string (STR) is used for partitioning using values such as public, PHS (Public Health Service) and DOD (Department of Defense) where DOD is considered secure and public not secure. A projection date, for example to the year, partitions each key_date. If the two horizontal partitioning fields, generator_class and key_date, are not defined, their fields default to PHS and the current year respectively.

Partitioning is performed for data security and performance. Each type of generator_class partition can be located on a different server for physical separation of data, anomalies, cases, and alerts.

The invention may receive anomalies generated by different algorithms from diverse entities. Each anomaly generator_identifier is recognized from a list of registered generators such as from the OIG (Office of the Inspector General) or other anomaly generator sources. Each anomaly generator has its own key_date and key_string combination.

The invention provides a warning message to those users when an anomaly is loaded with the same four key fields—generator_class, generator_identifier, key_date, and key_string—as an anomaly previously loaded.

For cases, generator_class is the case manager and generator_identifier has the default value of the invention. key_string is a sequence number internally generated by the case manager.

Common Location Fields location_class (STR)
location_type (STR)
location_count (INT)
location (STR)

The location_class data entry is "pat" when the locations are those of the patient and "acc" when the locations are those of the provider. Valid location_types include zip5, zip3, state, metropolitan statistical area (MSA), region, US, etc. A location may include a radius suffix such as zip5_4, where _4 includes each zip5 within 4 miles of a given location. Other location types are added as the data sources expand.

A region is defined as a set of zip5's or any other set of locations. For example, NYC Metro, Manhattan N.Y., LabsFP_10, and others. Therefore, a zip5region table, part of the metadata of the case manager, defines one or more regions as multiple zip5's.

An alternative data structure allows recursive definitions where the region table has four fields, parent_name, parent_type, child_name, child_type. When a location_count integer (INT) is greater than 1, one or more locations are separated by commas. Alternatively, a region may be defined in zip5region or region.

Each data element, and therefore each anomaly, will typically have two sets of locations—the patient location and the provider or account location. The patient location may be the patient's home residence or temporary address if the patient is traveling. The provider location can be the location of the treating physician's office, the hospital emergency department, or the laboratory testing center. For detailed investigation of a case, both locations may be important to the investigation. For purposes of defining an anomaly and a case, either the patient or the account location may be important. When both locations are significant, either the patient or account location should be taken as primary for the location_class and the other entered in another field, such as covariates, generator_identifier, algorithm, or notes. It is not necessary to have different sets of location fields for patient and account.

Common Medical Condition Fields medical_domain (STR)
medical_class (STR)
medical_sub_class (STR)

The medical domain specifies the source of the data, and thus the content for the medical fields. For example, within the domain of the laboratory records, medical_class is a test group, and medical_sub_class is a test type. medical_sub_class can be refined, such as:

medical_class Respiratory
    medical_sub_class Strep, Group A
medical_class Respiratory
    medical_sub_class Strep, Group A: Culture, Throat
medical_class Respiratory
    medical_sub_class Strep, Group A:AG
medical_class can similarly be refined.

Common Covariate Fields covariate_string (STR)

Covariates, such as age and gender, are encoded in the covariate_string as comma-separated key-value pairs. Selected covariates, namely location, medical condition, and date range have reserved fields. The covariate_string key-value pair construction permits flexibility in recording additional covariates. Medical condition may contain a restriction to particular age and gender.

Common Date and Date Range Fields earliest_record (DC)
latest_record (DC)
days (FLT)

The date clocks (DC) for the earliest record and latest record are approximate only. The operational definition is that the anomaly notification generator should insert values for a range that includes a high fraction, for example 80% of patients suspected, when the algorithm was run, to be impacted by the medical condition. The latest record is likely to be better defined than the earliest record when an outbreak is beginning. A comment on the values used for the earliest and latest record date clocks may be included in a notes field (described below). The number of days between earliest and latest records is recorded as a decimal fraction.

As alternatives to date clocks and floating-point (FLT), earliest and latest records and days might be recorded as dates (without time of day) and integer number of days (rounded up) respectively. The greater resolution is preferable unless system performance suffers.

Common Impacted Counts Fields impacted_per_day (FLT)
impacted_count (INT)
population_count (INT)
priority (FLT)

The number of impacted, population count, and rate of infection, impacted per day, are approximate. impacted_count may be the number of distinct patients between the earliest and latest records. impacted_per_day is the ratio of impacted_count to the day's field. population_count is taken from a census or other comparison. For example, the total number of laboratory test requisitions that include a respiratory test between the earliest and latest records. A comment on values used might be included in the notes field. Anomaly or case priority is a floating-point number in the range 0-100.

Common Security Fields access_level (STR)
access_zone (STR)

In addition to the security control provided by generator_class, access_level describes data sensitivity, i.e., a 0 for public data summaries and a 1 for the default, for HIPAA protected data. access_zone is a location designation which may be a state or one or more defined geographical regions. A more general specification would code access as a list-valued field, with child values comprising a set of access level and access zone pairs.

Case Manager Logic

As discussed above, received anomalies are organized into cases. An anomaly can belong to more than one case. The invention comprises four approaches to organizing anomalies into cases, cases into master cases, and presenting to a user a case work list.
 a) Direct mapping, where a case has the same common fields as an anomaly.
 b) Generalizations, where one or more common fields for a case are more inclusive than for an anomaly.
 c) Master case, where a case contains other cases.
 d) Work list, contains cases in the case manager selected according to various criteria.

An AnomalyCase table specifies which anomalies belong to which cases. An AnomalyCaseMap table specifies the mappings involving generalization and master cases.

Anomaly, Case and AnomalyCase

Each received anomaly belongs to one or more cases. This membership is defined in the AnomalyCase table, which combines the five key fields of each of Anomaly and Case with an additional relevance field.
 anomaly_generator_class (STR) case_generator_class (STR)
 anomaly_generator_identifier (STR) case_generator_identifier (STR)
 anomaly_key_date (DATE) case_key_date (DATE)
 anomaly_key_str (STR) case_key_str (STR)
 anomaly_descriptor (STR) case_descriptor (STR)
 anomaly_relevance (STR) case_relevance (STR)

Default data values for the case_ and anomaly_generator classes are both PHS, and for the case_generator_identifier is the invention. For a master case, the anomaly fields in AnomalyCase may contain the identifying key for a case. The case_descriptor field is set to an "a" and the anomaly_descriptor field is set to a "c" for a case.

relevance is a descriptive string that may have specific meaning. relevance defaults to a " ", which indicates 100% or fully relevant. A numeric value in the range 0-100 or a numeric value with a following "%" is understood to represent percentage relevance. Thus the default " " relevance is 100%.

relevance may take the form of a distance. For example, if the anomaly and the case are each defined by a single zip5, and the zip5 in the anomaly is centered 4.5 miles from the zip5 in the case, then the string will be "4.5 m". On a scale where "0 m" is 100% relevance and "10 m" is 0% relevance, "4.5 m" may translate to 55% relevance.

Illustrative Rules for Case Membership—AnomalyCaseMap

The generator_class will be the same, with certain exceptions to be defined, for a case and for each anomaly belonging to that case. If a case already exists and is not retired, then the anomaly is added to that case. Otherwise a new case is created. Creation of master cases from existing cases follows.

In each of the following rules, it is required that an anomaly belongs to a case only if the generator_class of the case is equal to the generator_class of the anomaly, or if the generator_class of the anomaly is a generic, which is more general. The covariates included in the covariate_string in the anomaly either are each equal to or at least as specific as the respective covariates in the case.
 A) An anomaly belongs to a case having the same location and medical fields.
 B) An anomaly belongs to each case having the same location and with medical field or fields that singularly, or collectively, is an ancestor of the anomaly's medical field set. For example, for lab test data, all anomalies with a given test group will belong to the case with that test group and any test type.
 C) An anomaly belongs to each case with the same medical fields and with location that contains the anomaly's location. The set of locations to consider include zip3, state, MSA, and any regions listed in zip5region and region. There are also two locations that include other zip5's within 10 miles, which are listed in zip5nbr. These locations are: zip5 disk for which each zip5 within 10 miles of the given zip5 has full relevance; zip5 neighborhood for which the relevance of each zip5 within 10 miles has relevance decreasing with distance. The zip5 disk and zip5 neighborhood differ in the way the date and count fields for anomalies combine to the corresponding fields for the cases.

D) An anomaly belongs to each case with a location that contains the anomaly's location, and with a medical field set that is an ancestor of the anomaly's medical field set.

The AnomalyCaseMap table lists the alternatives under A)-D), and includes a map status field that indicates when the mapping should be active.

Master Cases

Cases contain anomalies and Master Cases contain cases. The Case table contains both versions. The case_descriptor field in the Case table and the case_descriptor field in the AnomalyCase table take the value "a" for an anomaly-containing case and "c" for a master case.

Rules for creating master cases follow and are listed as separate entries in AnomalyCaseMap. Additionally, users with the necessary permissions can combine one or more cases manually into a master case.

Rules for Combinations of Common Fields

The discussion of rules centers on cases containing anomalies. The date set of common fields for the case has as earliest record the earliest record taken across any anomaly that belongs to the case provided that the anomaly is fully relevant. The same rule holds for latest record. The days for the case are the difference between latest record and earliest record.

An alternative is to ignore in the date set calculation any anomaly that is more than two weeks older. For example, the case's most recent anomaly. The impacted set of common fields for the case follows relatively complex rules for combinations. As time elapses since case creation, increasing numbers may be impacted, and the anomalies may include an expanding geographical region, for example to include a greater number of zip5's within the given zip3, msa, state, region, or zip5 disk, but not necessarily all such zip5s within the given region.

Considerations are:
i) Not to double-count either impacted or population, if the date range of two anomalies overlaps or the locations of two anomalies overlap.
ii) To reset the impacted number by direct query of the result data, bypassing the counts included in the anomaly notifications and updating previous counts.
iii) To match the population count to the same geography as the impacted count, regardless of whether population is known more completely.

The case manager is a tool that supports investigation. The combination values for the common fields are intended to give sensible initial indications. However, due to ambiguities in combining values of common fields across anomalies, an investigator may drill down into the data and collect summary common field values explicitly. Impacted_per_day is the ratio of impacted count to days, provided those two quantities are consistent within one another.

Case priority may be computed from data bypassing the anomaly priorities. For other situations, rules for using and combining the priorities of one or more anomalies are needed. It is unlikely that a reasonable routine for resolving overlaps is possible; therefore, a weighted average of priorities is calculated.

Weighting factors are a product of:
1. relevance, where any numeric value between 0 and 100 is considered a percentage and a distance d miles is transformed to $$100 \times \left(1 - \frac{d}{10}\right)\%;$$

2. impacted_per_day; and
3. a factor that varies inversely with time whenever the anomaly is older than 1 week and less than 2 weeks.

The security set of common fields for a case may follow a permissive logic, where summary information is combined into the case but access to the anomaly continues to be governed by the security of that anomaly.

Case Aging

A case may be active, open, locked, closed, retired provisionally, or retired. A case is said to be worked if it is opened and subsequently closed. Additionally, a case may have three flags: visited, recycled, and review.

The initial state of a case is active. A case may be viewed in a read-only mode at any time provided that the user has the necessary permissions. A case is opened to be worked by an investigator, and then may be closed by the investigator. Optionally, an investigator with the appropriate permissions can lock an already open case to prevent anyone else from interfering with the work in progress. When the case is unlocked, then it becomes open again, unless it is immediately closed.

Initially, a case is unvisited. When a case is viewed, or it is opened, locked, or closed, a visited flag is set. A review flag is set on an unvisited case that is not visited within some interval of time.

When activity ceases on a case, either because the case is closed or because no further anomalies are added to the case, the case is provisionally retired. If an anomaly is received when a case is provisionally retired, the case becomes active again. A recycled flag is set.

A case that has been provisionally retired for some interval of time becomes retired. If an anomaly is received when the case is retired, a new case is generated.

Users with the necessary permissions can manually change the status of a case from retired to active. An alternative is to manually link cases, including retired cases, in a master case.

Some parameters governing case aging, with sample values, include the following:
1) a case is retired provisionally 7 days after the most recent anomaly or 3 days after the case is closed, whichever comes sooner;
2) a case is retired 5 days after it is retired provisionally;
3) a case that remains open for 14 days or longer is closed automatically;
4) a case that remains locked for 14 days or longer is closed automatically; and
5) the review flag is set on an unvisited case no more than 5 days after the most recent anomaly or no more than 14 days after case creation, which ever comes sooner.

Monitoring

The invention monitors:
the number of anomalies loaded daily;
the current and historical distribution of cases;
the distribution of cases that are active, open, locked, closed, retired provisionally, and retired;
the disposition of cases; and
the distribution of cases with flags set.

Table Schema

The fields not included in the six sets of common fields—key, location, medical, dates, counts, security—are as follows:

Case

The Case fields include, but are not limited to timestamps and user identifiers associated with the case manipulation and case status.
    element_count (INT)
    case_descriptor (STR)
    case_status (STR)
    case_flag (STR)
    alert_status (STR)
    creation_timestamp (DC)
    lock_timestamp (DC)
    locker_identifier (STR)
    system_timestamp (DC)
    change_timestamp (DC)
    changer_identifier (STR)
    case_tag (STR)
    open_timestamp (DC)
    retire_timestamp (DC)
    retire_reason (STR)
    note (STR)

Anomaly

The Anomaly table includes fields for descriptions related to the type of anomaly and the algorithm, three different severity measures and their descriptions, and unspecified STR fields.
    anomaly_status (STR)
    receipt_timestamp (DC)
    generation_timestamp (DC)
    system_timestamp (DC)
    anomaly_type (STR)
    algorithm (STR)
    algorithm_parameters (STR)
    algorithm_description (STR)
    severity_measure_1 (FLT)
    severity_measure_1_description (STR)
    severity_measure_2 (FLT)
    severity_measure_2_description (STR)
    severity_measure_3 (FLT)
    severity_measure_3_description (STR)
    note (STR)
    anomaly_1 (STR)
    anomaly_2 (STR)
    anomaly_3 (STR)
    anomaly_4 (STR)
    anomaly_5 (STR)
    anomaly_6 (STR)
    anomaly_7 (STR)
    anomaly_8 (STR)
    anomaly_9 (STR)
    anomaly_10 (STR)

In one embodiment, the invention is deployed as a network-enabled framework and is accessed through a graphical user interface (GUI). The application resides on a server or a plurality of servers and is accessed by users via a client application, such as a web browser (Mozilla Firefox, Netscape, Microsoft Internet Explorer, and others) or via another client access software application that is not a general-purpose browser. This access takes place over a network or the Internet using custom or standard Internet languages and protocols, and may involve scripting languages including HTML, dynamic HTML (DHTML), Microsoft VBScript (Visual Basic Scripting Edition), Jscript, ActiveX and Java. A user's client application contacts a server hosting the application and requests information or resources. The server locates, and then sends the information to the client application which displays the results to the user.

Figure 2:
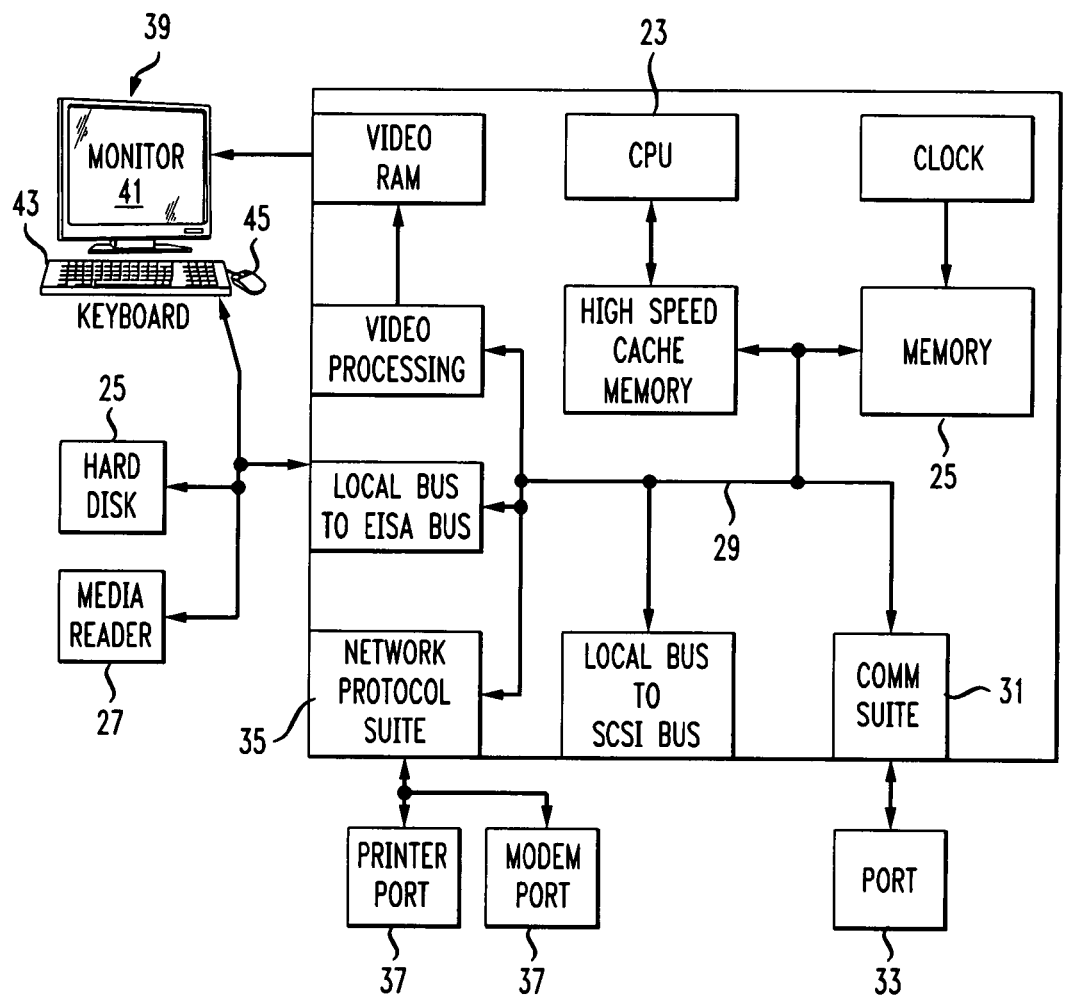
FIG. 2 is a block diagram of an exemplary computer.

An embodiment of a computer 21 executing the instructions of an embodiment of the invention is shown in FIG. 2. A representative hardware environment is depicted which illustrates a typical hardware configuration of a computer. The computer 21 includes a CPU 23, memory 25, a reader 27 for reading computer executable instructions on computer readable media, a common communication bus 29, a communication suite 31 with external ports 33, a network protocol suite 35 with external ports 37 and a GUI 39.

The communication bus 29 allows bi-directional communication between the components of the computer 21. The communication suite 31 and external ports 33 allow bi-directional communication between the computer 21, other computers 21, and external compatible devices such as laptop computers and the like using communication protocols such as IEEE 1394 (FireWire or i.LINK), IEEE 802.3 (Ethernet), RS (Recommended Standard) 232, 422, 423, USB (Universal Serial Bus) and others.

The network protocol suite 35 and external ports 37 allow for the physical network connection and collection of protocols when communicating over a network. Protocols such as TCP/IP (Transmission Control Protocol/Internet Protocol) suite, IPX/SPX (Internetwork Packet eXchange/Sequential Packet eXchange), SNA (Systems Network Architecture), and others. The TCP/IP suite includes IP (Internet Protocol), TCP (Transmission Control Protocol), ARP (Address Resolution Protocol), and HTTP (Hypertext Transfer Protocol). Each protocol within a network protocol suite has a specific function to support communication between computers coupled to a network. The GUI 39 includes a graphics display such as a CRT, fixed-pixel display or others 41, a key pad, keyboard or touchscreen 43 and pointing device 45 such as a mouse, trackball, optical pen or others to provide an easy-to-use, user interface for the invention.

The computer 21 can be a handheld device such as an Internet appliance, PDA (Personal Digital Assistant), tablet PC, Blackberry device or conventional personal computer such as a PC, Macintosh, or UNIX based workstation running their appropriate OS (Operating System) capable of communicating with a computer over wireline (guided) or wireless (unguided) communications media. The CPU 23 executes compatible instructions or software stored in the memory 25. Those skilled in the art will appreciate that the invention may also be practiced on platforms and operating systems other than those mentioned.

A communications network can be a single network or a combination of communications networks including any wireline, wireless, broadband, switched, packet or other type of network through which voice or data communications may be accomplished. Networks allow more than one user to work together and share resources with one another. Aside from distributed processing, a network provides centralized storage capability, security and access to resources.

Network architectures vary for LANs (Local Area Networks) and WANs (Wide Area Networks). Some examples of LAN network architectures include Ethernet, token ring, FDDI (Fiber Distributed Data Interface) and ATM (Asynchronous Transfer Mode). The capability of individual computers being linked together as a network is familiar to one skilled in the art.

Figure 3:
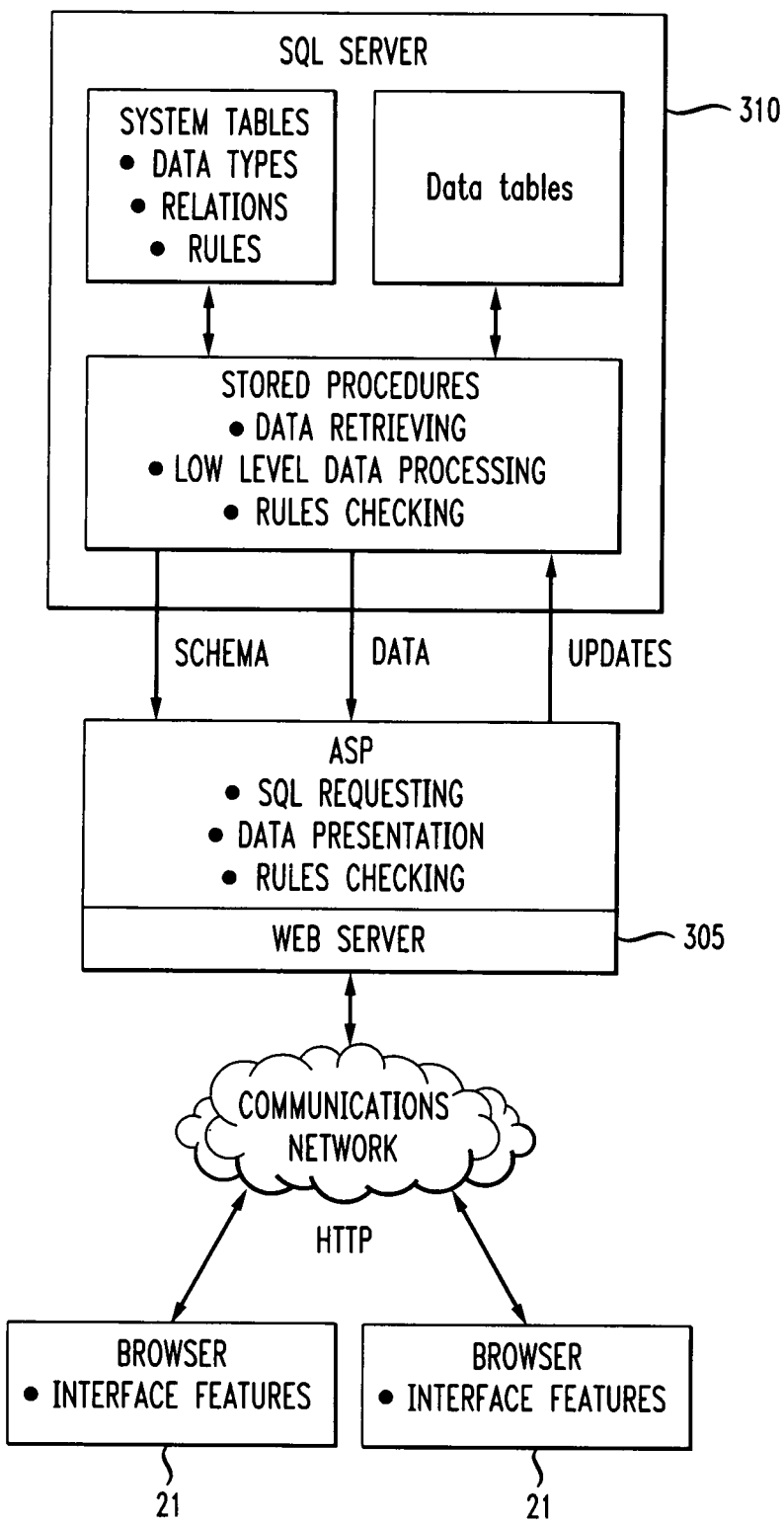
FIG. 3 is an exemplary application architecture.

Since the application is built using Web-based technology and is available everywhere, users having authorized access can access the network data through a browser or other client access application as shown in the application architecture 300 shown in FIG. 3. Individual computers 21 at a plurality of locations can communicate with a plurality of Web servers 305, which in turn communicate with a database server 310 hosting the application. A communication path is established between the client application executed on a computer 21 and the database server 310 through an application (such as Active Server Pages) environment using Web servers 305. The database server 310 executes the application and serves as the repository for all database information.

Figure 4B:
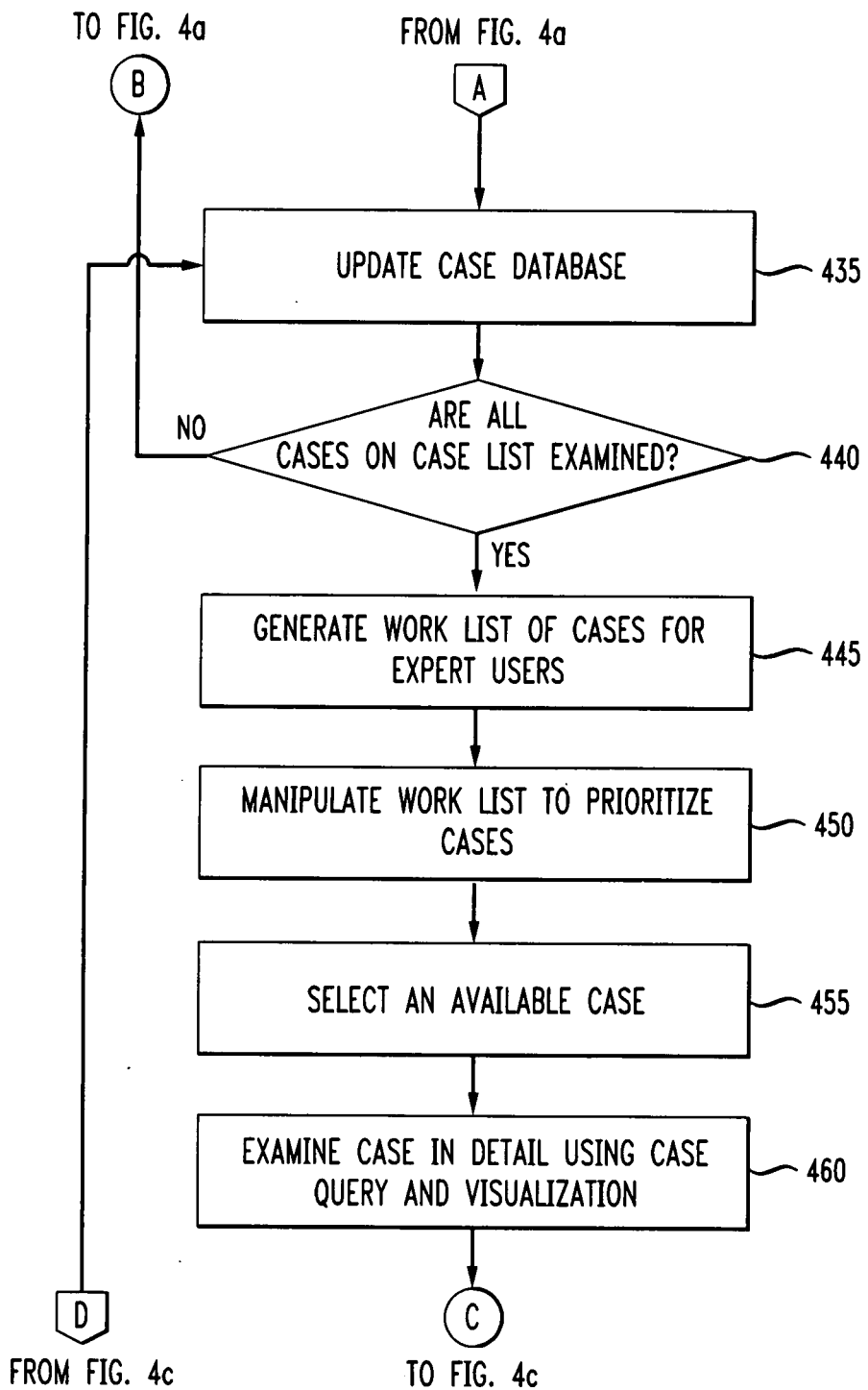
Figure 4C:
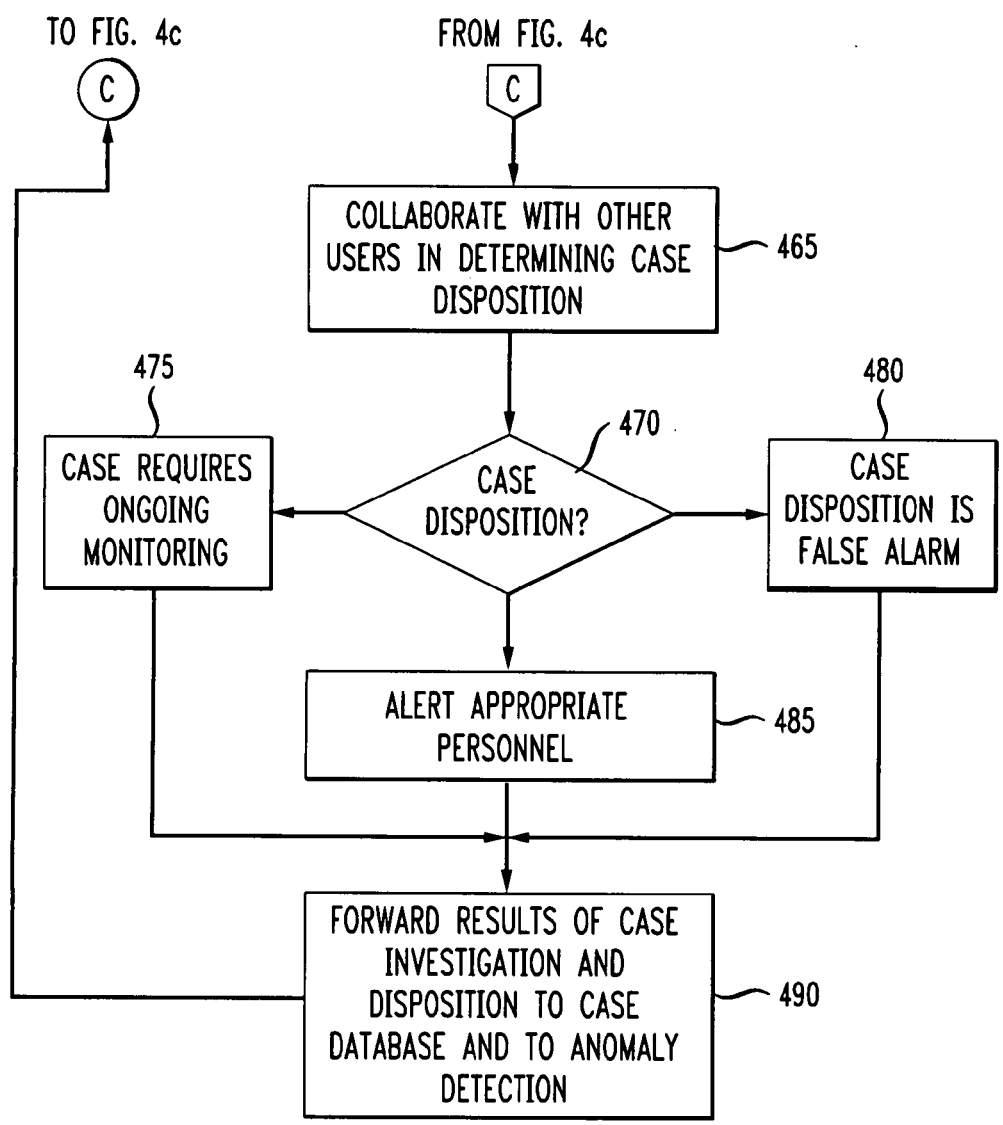
Figure 5:
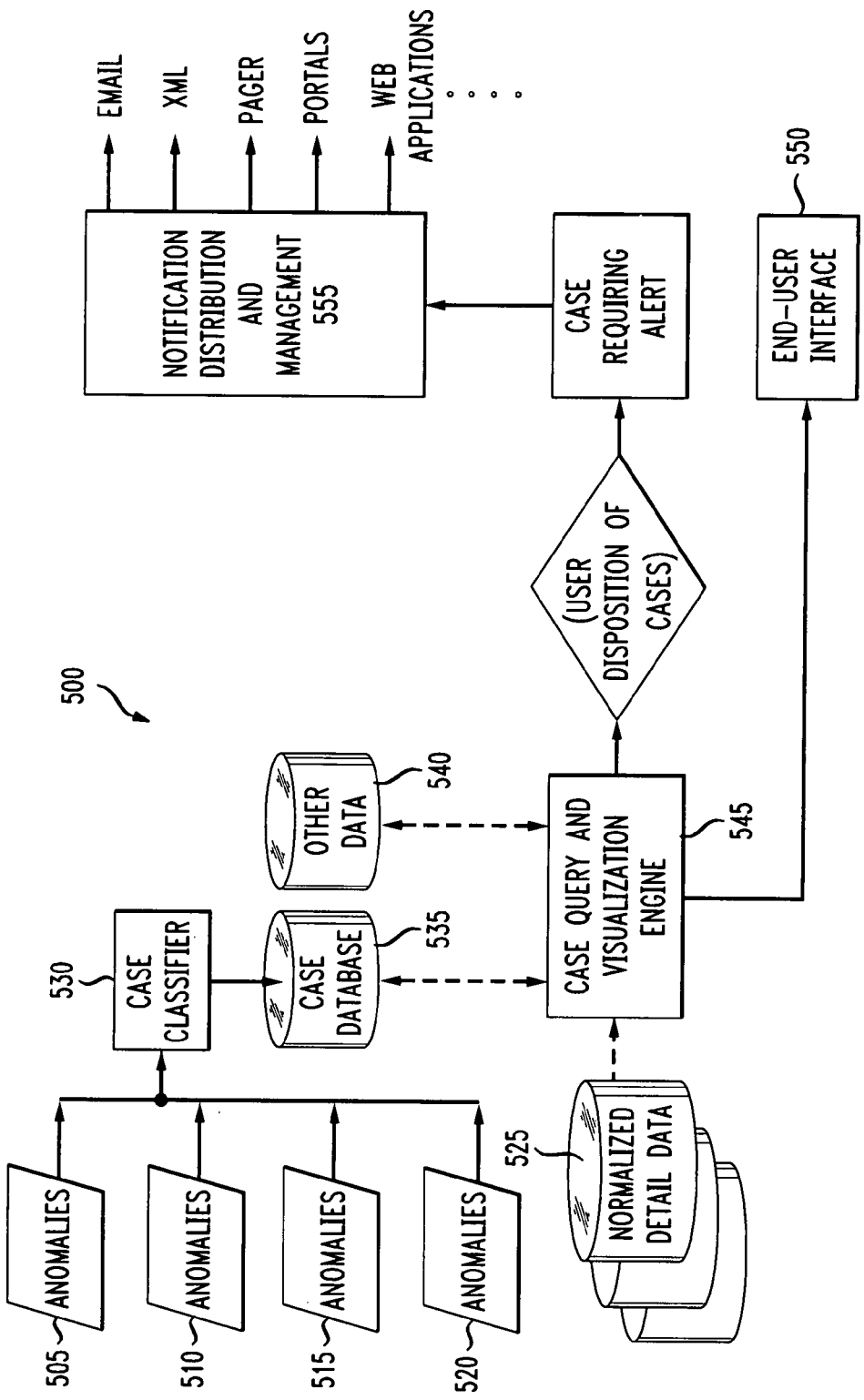
FIG. 5 is an exemplary framework of the individual modules of the invention.

Shown in FIGS. 4a, 4b and 4c is a flowchart of the case manager method according to one embodiment of the invention. Shown in FIG. 5 is a corresponding framework 500 of the various modules that comprise the invention as executed in the data center server 310. Preferably, the invention framework 500 is secure and allows effective integration of database information, external Web Services, and health and regulatory agency information through a set of coupled software modules. The invention framework allows effective management and disposition of received anomalies and shows data flow through the set of modules comprising the invention. The modules include external system gateways 505, 510, 515, 520, a normalized detail data store 525, a case classifier 530, a case database 535, a data store for other information such as census data, geographical coordinates, etc. 540, a case query and visualization engine 545, an end-user interface 550, and a notification and distribution manager 555.

The external system gateways 505, 510, 515, 520 are software modules that accept anomaly information provided by early event detection models co-resident on the same CPU with the case manager or via the network. The anomalies can be accepted from any anomaly generator, third party, or Web Service(s), and converts and normalizes the data 525 into a compatible format for the case manager framework 500 (step 400).

The gateways 505, 510, 515, 520 support XML (eXtensible Markup Language) and other markup languages, and can normalize received data to an XML format or Java class before forwarding to the case classifier 530. Gateways are used for the case manager framework 500 to receive anomalies provided by early detection models generated by external systems. Each gateway accepts anomaly data generated from associated external system, such as government agency DOD sites, a site or a plurality of sites pertaining to medical, pharmaceutical, regulatory, and others. Upon receiving and normalizing anomaly information, each gateway forwards the information to the case classifier 530.

The case classifier 530 executes the case manager application logic. Each received anomaly notification (step 400) is loaded into an anomaly database (step 405). The case classifier 530 classifies each received anomaly using the rules for case membership discussed above. The case classifier 530 enumerates a list of cases (step 410), and the anomaly is assigned to each case on the list as follows. The case classifier 530 loops over each case on the list (steps 415-440). For each case on the list, the classifier 530 determines whether a case exists (step 420). If a case does not exist, a new case is created (step 425). The anomaly is added to the new or existing case (step 430) and the case database is updated with the information for that case (step 435). Each case enumerated on the list of cases is examined (step 440).

Periodically, at the request of a user, or in response to a signal, such as a case database update, the case manager queries the case database to generate a work list of cases (step 445). The work list is specific to a user, and is further customized according to parameters set by and for the user. For example, the work list may contain cases that relate to a particular medical condition, for example, the flu, or to a particular geographical region, or to both and include only new cases (that have not previously been looked at) or recycled cases (that have previously been looked at). The user will manipulate the work list (step 450) to help prioritize the cases on the work list. The work list might be sorted by one or more variables including recency (the date of last update), impact (size of patient population), and confirmation (number of included anomalies and related statistics).

The case manager 500 provides for the integration and close collaboration of entities. The manager permits users to specify their interest in a particular event and attach conditions that must be met and actions that need to be taken, as and when their event of interest happens. The notification and distribution manager 555, in conjunction with the case query and visualization engine 545 and end-user interface 550, is an intelligent rule-based notification engine which routes information to its destination based on user subscription, presence, availability, and other parameters through a variety of channels, enabling a versatile two-way communication path between entities. It facilitates a constant communication between the expert users.

The manager 500 dispositions each received anomaly in detail via the case query and visualization engine 545 and end-user interface 550. Typically, a user will select a case to work from the prioritized work list (step 455). The details for that case are provided for collaboration with various expert users such as data experts, statisticians, public health officials, epidemiologists and others, in order to disposition received anomalies (steps 460, 465).

During collaboration with the external entities, case disposition typically takes one of either three paths (step 470). The case requires ongoing monitoring (step 475); the case is deemed a false alarm (step 480); or an alert is issued and appropriate entities are contacted using the plurality of communication channels via the notification manager 555 (step 485). The case manager 500 routes information to multiple devices and others with two-way communication capability. It contains abstract notification rules that can select one or multiple relevant targets and notify them via various channels.

After a case determination is made, all collaboration results are stored in the case database 535 and associated tables 540 for further use when analyzing future received anomalies (step 490).

FIGS. 3 and 5 show the structure of one embodiment of the invention. Since the case manager is built using Web-based technology and in one embodiment is an HTML based Web-enabled utility, an Internet browser using a communications network can access the application. Individual computers 21 at a plurality of locations can communicate with the Web server layer 305 of the application server hosting the application. The server 310 stores operational instructions for the application, database fields, regulatory requirements, preferred modes of contact for expert users, and other storage needs.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for mediating anomaly notifications in health data, comprising:
    performing on a computer:
        receiving anomalies generated by different algorithms, with each anomaly in the anomalies comprising anomaly variable data;
        comparing fields in one of the anomaly variable data to a table defining cases;
        assigning one of the cases to the one anomaly variable data when a field in the one anomaly variable data matches an entry in the table;
        determining a distance between the one anomaly variable data and the one case;
        assigning a relevance to the one anomaly variable data based upon the distance;
        adding a relevance field to the one anomaly variable data;
        assigning the relevance to the relevance field;
        associating in the table the one case to the one anomaly variable data;
        providing an interactive environment for collaboration among multiple users;
        dispositioning the one case based upon results of the collaboration; and
        retiring the one case.

2. The method according to claim 1, further comprising retrieving a default value for the field in the one anomaly variable data.

3. The method according to claim 1, wherein the fields in the one anomaly variable data comprise a case descriptor field having a text value set to "a."

4. The method according to claim 1, further comprising determining whether the one anomaly variable data belongs to the one case.

5. The method according to claim 1, further comprising mapping the one anomaly variable data to a different case.

6. The method according to claim 5, further comprising updating the one case.

7. The method according to claim 1, further comprising assigning a zone improvement plan code to the relevance.

8. The method according to claim 1, further comprising organizing multiple anomalies into the one case.

9. The method according to claim 1, further comprising defining the relevance as a percentage.

10. The method according to claim 1, further comprising defining the relevance according to a zone improvement plan.

11. The method according to claim 1, further comprising defining the relevance as a number in a range of 0-100.

12. The method according to claim 1, further comprising creating the table that associates the one anomaly variable data to the cases.

13. The method according to claim 1 further comprising decreasing the relevance as the distance increases.

14. The method according to claim 1, further comprising notifying collaboration entities.

15. The method according to claim 1, further comprising creating an event table corresponding with the one case wherein actions taken upon the one case are recorded as an event.

16. The method according to claim 1, wherein dispositioning the one case comprises closing the one case.

17. A method for mediating anomaly notification in health data, comprising:
    receiving anomalies generated by different algorithms, with each anomaly comprising anomaly variable data;
    comparing fields in one of the anomaly variable data to a table defining cases;
    determining a match between a field in the one anomaly variable data and an entry in the table;
    assigning one of the cases in the table to the one anomaly variable data based on the match;
    determining a distance by a processor between the one anomaly variable data and the one case;
    assigning a relevance to the one anomaly variable data based on the distance;
    adding a relevance field to the one anomaly variable data;
    assigning the relevance to the relevance field;
    associating the one case to the one anomaly variable data and to the relevance in the table stored in memory;
    extracting health data records associated with the one case;
    providing an interactive environment for collaboration among multiple users;
    dispositioning the one case;
    alerting an entity in response to a disposition of the one case; and
    retiring the one case.

18. A system for mediating anomaly notification in health data comprising:
    a processor; and
    memory for storing an application stored in the memory that when executed causes the processor to perform operations, the operations comprising:
    receiving anomalies generated by different algorithms, with each anomaly including anomaly variable data;
    comparing fields in one of the anomaly variable data to a table defining cases;
    assigning one of the cases to the one anomaly variable data when a field in the one anomaly variable data matches an entry in the table;
    determining a distance between the one anomaly variable data and the one case;
    assigning a relevance to the one anomaly variable data based on the distance;
    adding a relevance field to the one anomaly variable data;
    assigning the relevance to the relevance field;
    associating in the table the one case to the one anomaly variable data and to the relevance;
    providing an interactive environment for collaboration;
    dispositioning the one case based upon results of the collaboration; and
    retiring the one case.

19. The system according to claim 18, wherein the operations further comprise notifying of the one case.

20. The system according to claim 18, wherein the operations further comprise notifying of the anomaly variable data.

* * * * *